United States Patent
Laing et al.

(10) Patent No.: US 8,660,646 B2
(45) Date of Patent: Feb. 25, 2014

(54) PERCUTANEOUS TIBIAL NERVE STIMULATOR

(75) Inventors: Brent Laing, Elizabethton, TN (US); John David Green, Elizabethton, TN (US)

(73) Assignee: Advanced Uro-Solutions, LLC, Elizabethton, TN (US)

( * ) Notice: Subject to any disclaimer, the term of this patent is extended or adjusted under 35 U.S.C. 154(b) by 0 days.

(21) Appl. No.: 13/523,965

(22) Filed: Jun. 15, 2012

(65) Prior Publication Data

US 2012/0323294 A1 Dec. 20, 2012

Related U.S. Application Data

(60) Provisional application No. 61/497,570, filed on Jun. 16, 2011.

(51) Int. Cl.
*A61N 1/00* (2006.01)

(52) U.S. Cl.
USPC .................................. 607/39; 607/40; 607/41

(58) Field of Classification Search
USPC ..................................................... 607/39–41
See application file for complete search history.

(56) References Cited

U.S. PATENT DOCUMENTS

| | | | |
|---|---|---|---|
| 5,258,906 A | 11/1993 | Kroll et al. | |
| 5,458,124 A | 10/1995 | Stanko et al. | |
| 6,049,789 A | 4/2000 | Frison et al. | |
| 6,493,588 B1 | 12/2002 | Malaney et al. | |
| 6,662,052 B1 | 12/2003 | Sarwal et al. | |
| 6,829,704 B2 | 12/2004 | Zhang et al. | |
| 6,966,000 B2 | 11/2005 | Zhang et al. | |
| 6,983,375 B2 | 1/2006 | Zhang et al. | |
| 6,990,434 B2 | 1/2006 | Minogue et al. | |
| 7,093,032 B2 | 8/2006 | Minogue et al. | |
| 7,113,894 B2 | 9/2006 | Minogue et al. | |
| 7,219,222 B1 | 5/2007 | Durbin et al. | |
| 7,349,856 B2 | 3/2008 | Ackermann et al. | |
| 7,421,516 B2 | 9/2008 | Minogue et al. | |
| 7,536,226 B2 | 5/2009 | Williams et al. | |

(Continued)

FOREIGN PATENT DOCUMENTS

WO 2011041526 4/2011

OTHER PUBLICATIONS

Wrenn, et al.: Incorporating Percutaneous Tibial Nerve Stimulation (PTNS) Into a Community Based Urology Practice; www.urotoday.com/overactive-bladder, Jun. 14, 2011.

*Primary Examiner* — Nicole F Lavert
(74) *Attorney, Agent, or Firm* — Wade R. Orr, Esq.; Luedeka Neely Group, P.C.

(57) ABSTRACT

A tibial nerve stimulation device including a percutaneous electrode for inserting adjacent a stimulation site of a patient and a neurostimulator unit attachable to a transcutaneous electrode configured to be applied to skin adjacent the stimulation site. The neurostimulator unit includes a pulse generator electrically coupled to the percutaneous needle electrode and transcutaneous electrode and a microcontroller in communication with the pulse generator for monitoring a number of available treatment credits and activating the pulse generator, each available treatment credit corresponding to a treatment session and the pulse generator operable to be activated for performing the treatment session when the number of available treatment credits is at least one. A computer system is operable to communicate with the microcontroller of the neurostimulator unit for receiving a treatment credit request and transmitting the number of treatment credits purchased to the microcontroller of the neurostimulator unit.

13 Claims, 6 Drawing Sheets

(56) References Cited

U.S. PATENT DOCUMENTS

| | | |
|---|---|---|
| 7,571,002 B2 | 8/2009 | Thrope et al. |
| 7,634,645 B2 | 12/2009 | Zhang et al. |
| 7,739,725 B1 | 6/2010 | Zhang et al. |
| 7,813,809 B2 | 10/2010 | Strother et al. |
| 7,894,913 B2 | 2/2011 | Boggs et al. |
| 7,962,416 B1 | 6/2011 | Durbin et al. |
| 2002/0120467 A1 | 8/2002 | Buanes |
| 2004/0215287 A1 | 10/2004 | Swoyer et al. |
| 2005/0165693 A1 | 7/2005 | Moritzen |
| 2005/0245840 A1 | 11/2005 | Christopherson et al. |
| 2006/0190048 A1* | 8/2006 | Gerber .................. 607/41 |
| 2007/0167992 A1 | 7/2007 | Carley |
| 2008/0140451 A1 | 6/2008 | Hedrick et al. |
| 2008/0221644 A1 | 9/2008 | Vallapureddy et al. |
| 2008/0300449 A1 | 12/2008 | Gerber et al. |
| 2009/0132018 A1 | 5/2009 | DiUbaldi et al. |
| 2009/0248578 A1 | 10/2009 | Pollock et al. |
| 2010/0114259 A1 | 5/2010 | Herregraven et al. |

* cited by examiner

PERCUTANEOUS TIBIAL NERVE STIMULATOR

CROSS-REFERENCE TO RELATED APPLICATION

This application claims priority to U.S. Provisional Application Ser. No. 61/497,570 filed Jun. 16, 2011, and entitled "Percutaneous Tibial Nerve Stimulator," the contents of which are incorporated by reference herein in its entirety.

FIELD

This disclosure relates to the field of nerve stimulators. More particularly, this disclosure relates to a percutaneous tibial nerve stimulator device for treating urinary symptoms and a system for providing payment for use of the device on a per-treatment session basis.

BACKGROUND

Nerve and muscle stimulation are used to treat a variety of medical conditions such as to reduce pain and to assist muscle and joint rehabilitation. Nerve stimulation has also been used for decades to control bladder function. Various approaches to bladder neuromodulation have been studied with stimulation of the pudendal, sacral, and tibial nerves found to be effective in controlling bladder function.

Percutaneous tibial nerve stimulation is a uniquely effective therapy for treating overactive bladder (OAB) and the associated symptoms of frequency, urgency, and urinary urge incontinence. It is a minimally invasive neuromodulation delivery method performed by placing a percutaneous needle electrode in the proximity of the tibial nerve, i.e., the stimulation site. A pulse generator and a transcutaneous electrode are electrically coupled to the needle electrode for providing current pulses to the stimulation site by passing current from the transcutaneous electrode to the percutaneous electrode.

One type of percutaneous tibial nerve stimulation system is described in U.S. Pat. No. 6,493,588 and is incorporated herein by reference. The system described in the '588 patent includes a pulse generator, a first lead wire electrically coupled to the pulse generator, a transcutaneous electrode electrically coupled to the first lead wire, a second lead wire electrically coupled to the pulse generator, and a percutaneous electrode needle electrically coupled to the second lead wire. During treatment, the transcutaneous electrode is positioned distal from the selected stimulation site on the surface of the skin. The percutaneous electrode needle is inserted through the skin in proximity of the tibial nerve. Current pulses traverse the internal stimulation site by passing from the transcutaneous electrode to the internal percutaneous electrode needle.

One problem with the system of the '588 patent was that the owners have had trouble implementing the system into a financially viable and profitable business model. In an attempt to solve this problem, the reusable lead wire system as described in the '588 patent was converted into a single use lead system as described, for example, in U.S. Pat. No. 7,536,226 and U.S. Pat. No. 8,046,082. While the advent of the single use lead system provides the ability to charge a patient/health care professional on a "per-treatment session" basis by requiring a new lead set to be used during each treatment session, the system requires perfectly operating leads to be wasted which leads to additional costs for the patient and manufacturer of the system. Further, the single use lead system is unable to determine whether a treatment session has been completed. Thus, if the treatment session was interrupted for any reason, the single use lead set would have to be replaced with a new lead set.

Another problem that exists with the Uroplasty devices is that the unit is bulky and requires two lengthy leads for connecting the electrodes to a hand-held controller unit.

What is needed therefore is a percutaneous tibial nerve stimulator system having reusable leads which provides the ability to charge a patient for each treatment session. In addition, a more compact and user friendly percutaneous tibial nerve stimulator system is desired.

SUMMARY

A nerve stimulation system is disclosed including a neurostimulator unit having a pulse generator for electrically coupling to a percutaneous needle electrode and a transcutaneous electrode. The percutaneous needle electrode has a leading end for inserting adjacent a stimulation site of a patient and the transcutaneous electrode is configured to be applied to skin adjacent the stimulation site of the patient. A microcontroller is in communication with the pulse generator for monitoring a number of available treatment credits and activating the pulse generator, each available treatment credit corresponding to a treatment session and the pulse generator operable to be activated for performing the treatment session when the number of available treatment credits is at least one. During the treatment session, the pulse generator generates current pulses that pass between the transcutaneous electrode and the percutaneous needle electrode for providing stimulation to the stimulation site. A computer system is operable to communicate with the microcontroller of the neurostimulator unit. The computer system is operable to receive a treatment credit request having purchase information including a number of treatment credits purchased, each treatment credit purchased corresponding to an available treatment credit, and transmitting the number of treatment credits purchased to the microcontroller of the neurostimulator unit.

According to some embodiments, the computer system includes a customer interface for submitting the treatment credit request. The neurostimulator unit is preferably dimensioned and configured to be removeably attached to the transcutaneous electrode.

In certain embodiments, each treatment credit purchased includes a unique serial number, the microcontroller being operable to transmit usage information to the computer system for monitoring usage of the purchased treatment credits by the neurostimulator unit based on the unique serial numbers. The neurostimulator unit may be linked to a unique identification number and the purchase information of the treatment credit request includes the unique identification number for authorizing the transmission of the number of treatment credits purchased to the microcontroller of the neurostimulator unit.

According to some embodiments, the treatment credit request may be transferred from the computer system to a portable digital storage device, the portable storage device connectable to the neurostimulator unit for transmitting the number of treatment credits purchased to the microcontroller of the neurostimulator unit. In other embodiments, the computer system communicates with the microcontroller of the neurostimulator unit wirelessly through one of radio frequency, Bluetooth, infrared, and a wireless internet connection. The computer system may also communicate with the microcontroller of the neurostimulator unit through a universal serial bus connection.

According to another embodiment of the disclosure, a nerve stimulation system includes a plurality of neurostimulator units. Each neurostimulator unit includes a unique identification number for identifying the neurostimulator unit, a pulse generator operable to be electrically coupled to a plurality of electrodes configured to be applied adjacent a stimulation site of a patient, and a microcontroller in communication with the pulse generator for monitoring a number of available treatment credits and activating the pulse generator, each available treatment credit corresponding to a treatment session and the pulse generator operable to be activated for performing the treatment session when the number of treatment credits available is at least one, the pulse generator generating current pulses during the treatment session that pass between the plurality of electrodes for providing stimulation to the stimulation site. A computer system receives a treatment credit request having purchase information including the unique identification number of one of the plurality of neurostimulator units and a number of treatment credits purchased, each treatment credit purchased corresponding to an available treatment credit, the computer system being operable to communicate with the microcontroller of the neurostimulator units for transmitting the purchase information to an appropriate neurostimulator unit based on the unique identification number included in the purchase information.

According to some embodiments, each unique identification number is linked to at least one customer account and the computer system includes a customer interface for accessing the customer account and submitting the treatment credit request.

According to yet another embodiment of the disclosure, a method for providing a reusable nerve stimulation system to treat incontinence is disclosed. The method includes the following steps: providing a computer system having a customer interface; providing a neurostimulator unit including: a pulse generator for electrically coupling to a transcutaneous electrode configured to be applied to skin adjacent the stimulation site of a patient and a percutaneous electrode having a leading end for inserting adjacent a stimulation site of a patient, and a microcontroller in communication with the pulse generator for monitoring a number of available treatment credits to the neurostimulator unit and for activating the pulse generator during a treatment session when the number of available treatment credits is at least one; receiving at the computer system a treatment credit request transmitted through the customer interface, each treatment credit request having purchase information including a number of treatment credits purchased, each treatment credit purchased corresponding to an available treatment credit; transmitting the number of treatment credits purchased to the microcontroller of the neurostimulator unit; and adjusting the number of treatment credits available to the neurostimulator unit based on the number of treatment credits purchased transmitted to the microcontroller of the neurostimulator unit.

According to some embodiments, the method further includes determining whether the number of available treatment credits is at least one; and activating the pulse generator based on a treatment session request when it is determined that the number of available treatment credits is at least one.

In certain embodiments, the method further includes transmitting usage information from the microcontroller to the computer system, the usage information including a number of treatment sessions performed; monitoring the usage information of the neurostimulator unit through the computer system; and providing the usage information to a customer through a customer interface of the computer system.

According to some embodiments, method further includes providing each treatment credit purchased with a unique serial number; monitoring usage information of each treatment credit purchased at the neurostimulator unit; transmitting the usage information from the neurostimulator unit to the computer system for each treatment credit purchased based on the unique serial number.

BRIEF DESCRIPTION OF THE DRAWINGS

Further advantages of the disclosure are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
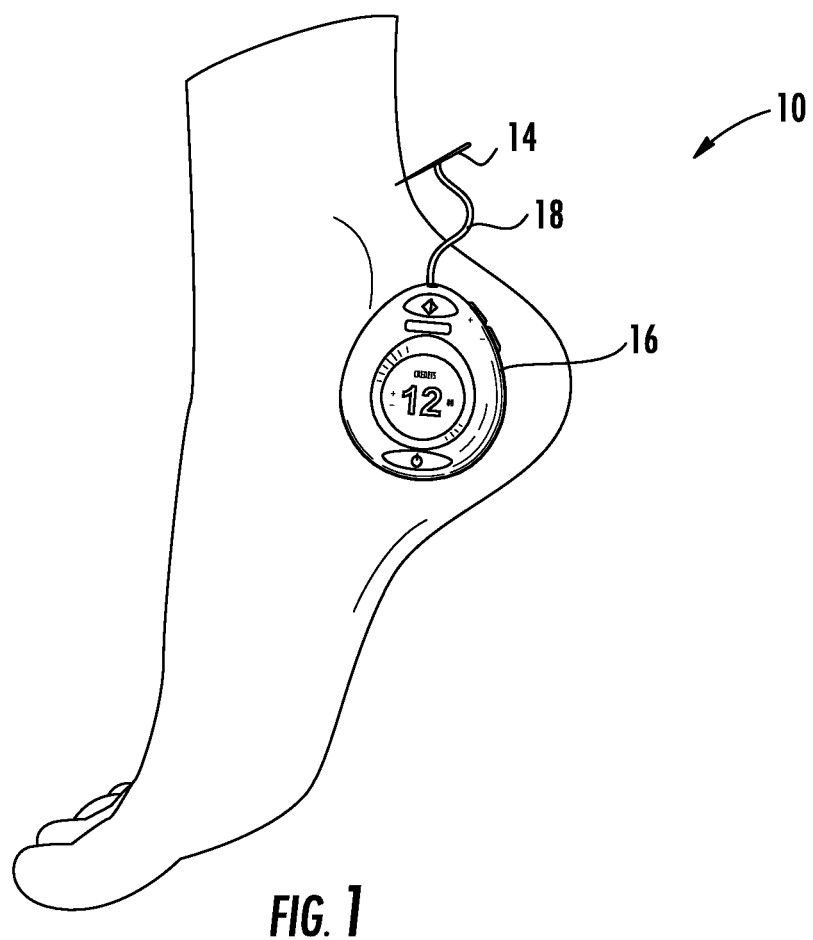
FIG. 1 is a view of the tibial nerve stimulation device applied to the patient according to one embodiment of the disclosure.

Referring to FIG. 1, a nerve stimulator device 10 includes a transcutaneous electrode pad (not shown), a percutaneous needle electrode 14, a battery operated neurostimulator unit 16 having a pulse generator, and a single lead wire 18 for electrically coupling the needle electrode 14 to the neurostimulator unit 16. In preferred embodiments, the neurostimulator unit 16 includes dimensions of approximately 54 mm in length, approximately 46 mm in width, and a depth of approximately 14 mm and is configured to be removeably attached to the electrode pad which is adhesively applied to a patient's skin. In other words, the neurostimulator unit 16 is sized and configured for comfortable placement of the unit adjacent the heel or ankle area of the patient.

Figure 3:
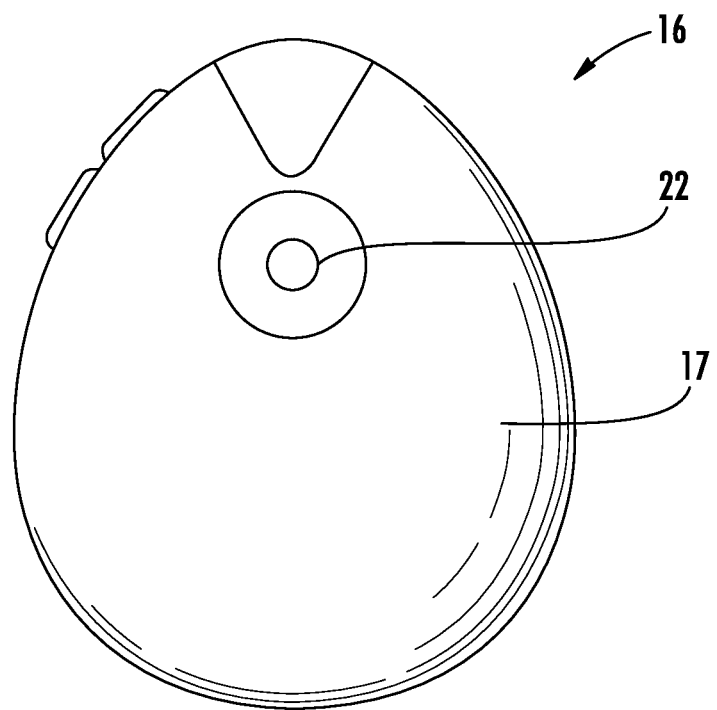
FIG. 3 is a rear view of a neurostimulator unit according to one embodiment of the disclosure.
Figure 4:
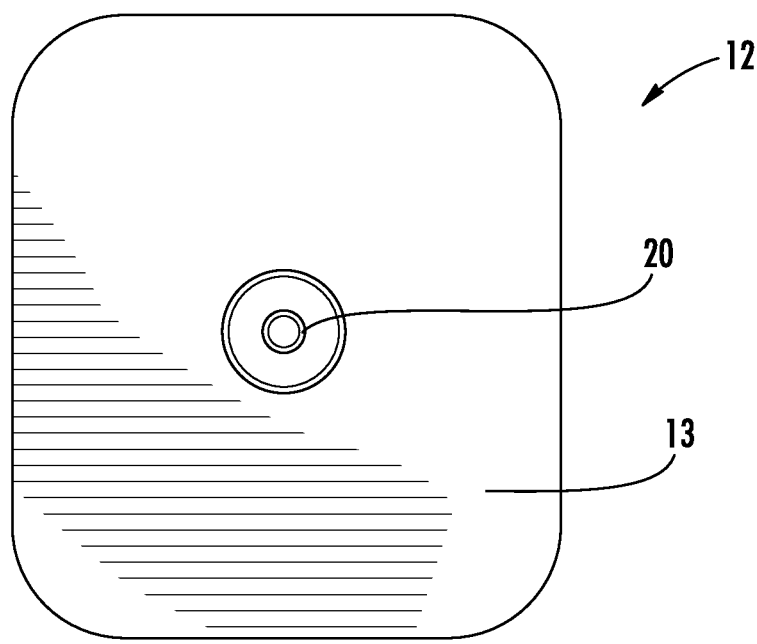
FIG. 4 is a front view of a transcutaneous electrode patch according to one embodiment of the disclosure.

Referring to FIGS. 3-4, the transcutaneous electrode pad 12 includes an attachment mechanism 20 on the top surface 13 of the pad 12 and the neurostimulator unit 16 includes a corresponding attachment mechanism 22 on the bottom surface 17 of the neurostimulator unit 16 for removeably attaching and electrically coupling the neurostimulator unit 16 with the electrode pad 12. In a preferred embodiment, the neurostimulator unit 16 includes a female snap connector 22 disposed on the bottom surface 17 that connects to a corresponding male connector 20 disposed on the top surface 13 of the electrode pad 12.

By providing a neurostimulator unit 16 having an integrated pulse generator and electrode pad 12 during operation of the stimulator device 10, only a single lead 18 is needed to be included in the device 10 to connect the needle electrode 14 and provide stimulation to the stimulation site. No lead wire is needed to electrically couple the neurostimulator unit 16 and electrode pad 12. This results in a compact system having very few parts. The entirety of the system is also able to be connected to the patient during treatment which provides the patient greater flexibility in movement during a treatment session. Further, as a hand held pulse generator is not being used, the single lead 18 only needs to be as long as the distance from where the electrode pad 12 is applied to the skin of the patient to the insertion site of the needle electrode 14.

In operation, the transcutaneous electrode pad 12 is positioned near a selected stimulation site on the surface of the skin. The percutaneous needle electrode 14 is then inserted through the skin adjacent the nerve or nerves to be stimulated, i.e., preferably adjacent the tibial nerve when treating incontinence. The neurostimulator unit 16 is attached to the transcutaneous electrode pad 12 and the lead wire 18 is connected to the neurostimulator unit 16 so that the pulse generator is electrically coupled to both the electrode pad 12 and the needle electrode 14. When the pulse generator is activated to perform a treatment session, current pulses traverse the stimulation site by passing from the transcutaneous electrode 12 to the internal percutaneous electrode needle 14.

Figure 2:
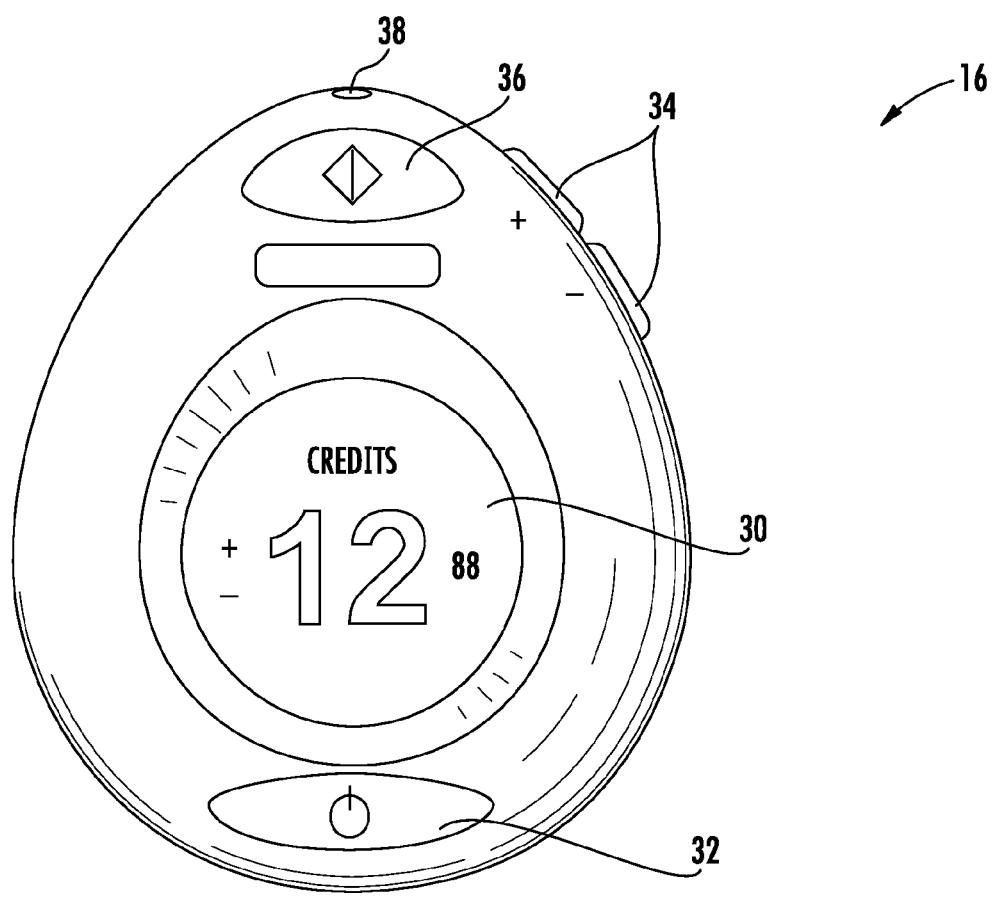
FIG. 2 is a front view of a neurostimulator unit according to one embodiment of the disclosure.

Referring to FIG. 2, the neurostimulator unit 16 includes a LCD display or other type of graphic display 30 for displaying operating information of the unit 16 such as the battery level, time remaining for a treatment session, signal strength of the pulse generator, treatment credits remaining for the unit 16, and a network/computer connection status. Further aspects of the neurostimulator unit may include, for example, operating utilities such as a power button 32 for turning the unit 16 on and off, a toggle control 34 for adjusting the signal strength of the pulse generator, a start button 36 for beginning a treatment session, and a receiver 38 for receiving the lead wire 18 and electrically coupling the percutaneous electrode 14 to the neurostimulator unit 16.

In alternate embodiments, the graphic display 30 and/or some of the operating utilities may be either removable or permanently separate from the neurostimulator unit 16 to allow for handheld control of the device 10. Such a design would provide for further compactness of the neurostimulator unit 16. The handheld unit would then preferably communicate with the neurostimulator unit 16 wirelessly using an infrared, Bluetooth, wireless internet, or other means of wireless connection. Alternatively, the handheld unit may include a wired connection with the neurostimulator unit 16. Other features of the handheld unit may include the ability to control multiple neurostimulator units 16 and the ability to time each treatment session and notify the patient or administrator with an audio alert at the end of the treatment session.

In another aspect of the disclosure, the neurostimulator unit 16 is preferably connectable to a computer system for providing a treatment credit purchasing system and for monitoring the status and usage of the device 10. The neurostimulator unit 16 is preferably operable to communicate with the computer system through a universal serial bus (USB) connector or wirelessly by using an infrared, Bluetooth, wireless internet, or other means of wireless connection. Alternatively, information may be transferred between the neurostimulator unit 16 and the computer system using a portable digital storage device such as a USB flash drive.

In these embodiments, the neurostimulator unit 16 includes a microcontroller or processor for storing information relating to the current status and past usage of the unit 16 and controlling operation of the device 10. The status and usage information may be transferred from the unit 16 to the computer system when the unit 16 is connected to the computer system. In particular, the microcontroller monitors a number of treatment credits the neurostimulator unit has available to it. Each available treatment credit corresponds to a treatment session. After a treatment session is completed, the number of available treatment credits is decreased. If there are no more treatment credits available to the neurostimulator unit 16, the microcontroller prevents the neurostimulator unit 16 from performing a treatment session by preventing activation of the pulse generator. In order for the unit 16 to be used in further treatment sessions, additional treatment credits must be purchased and transferred to the neurostimulator unit 16.

Figure 5:
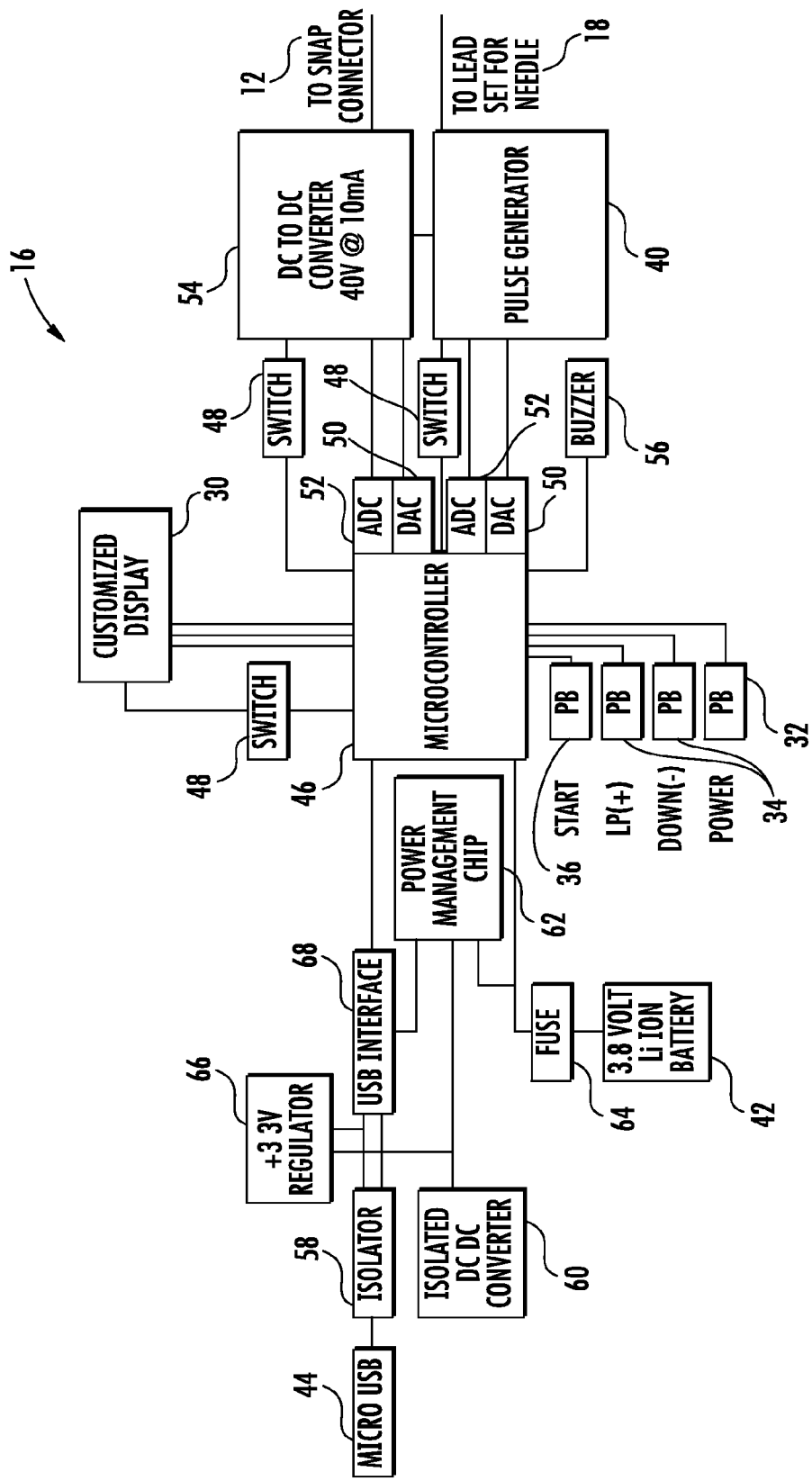
FIG. 5 is a block diagram of the internal circuitry of a neurostimulator unit according to one embodiment of the disclosure.

With reference to the block diagram of FIG. 5, one embodiment of the circuitry of the neurostimulator unit 16 is disclosed. As described above, the neurostimulator unit includes the graphic display 30, power button 32, toggle control 34, start button 36, pulse generator 40, battery 42, USB port 44, and microcontroller 46. The microcontroller 46 controls operation of the high voltage supply (DC to DC converter 54) and display of the operational characteristics on the graphic display 30 using a series of switches 48, digital-to-analog converters 50, analog-to-digital converters 52, and a DC to DC converter 54. A warning mechanism 56 such as a buzzer or light may be provided for notifying a patient or administrator that a treatment session is completed or a problem has occurred with the neurostimulator unit 16.

As shown, it is preferred that the USB port 44 is electrically isolated from the remaining components of unit 16 using an isolator 58 and isolated DC to DC converter 60. Other aspects of the unit 16 include a power management chip 62 disposed between the battery 42 and microcontroller 46, which uses power from the USB port 44 to charge the battery 44 connected through a fuse 64 disposed between the battery 42 and microcontroller 46. A regulator 66 is provided for maintaining a constant supply voltage to the USB interface 68 when the USB port 44 is connected.

Figure 6:
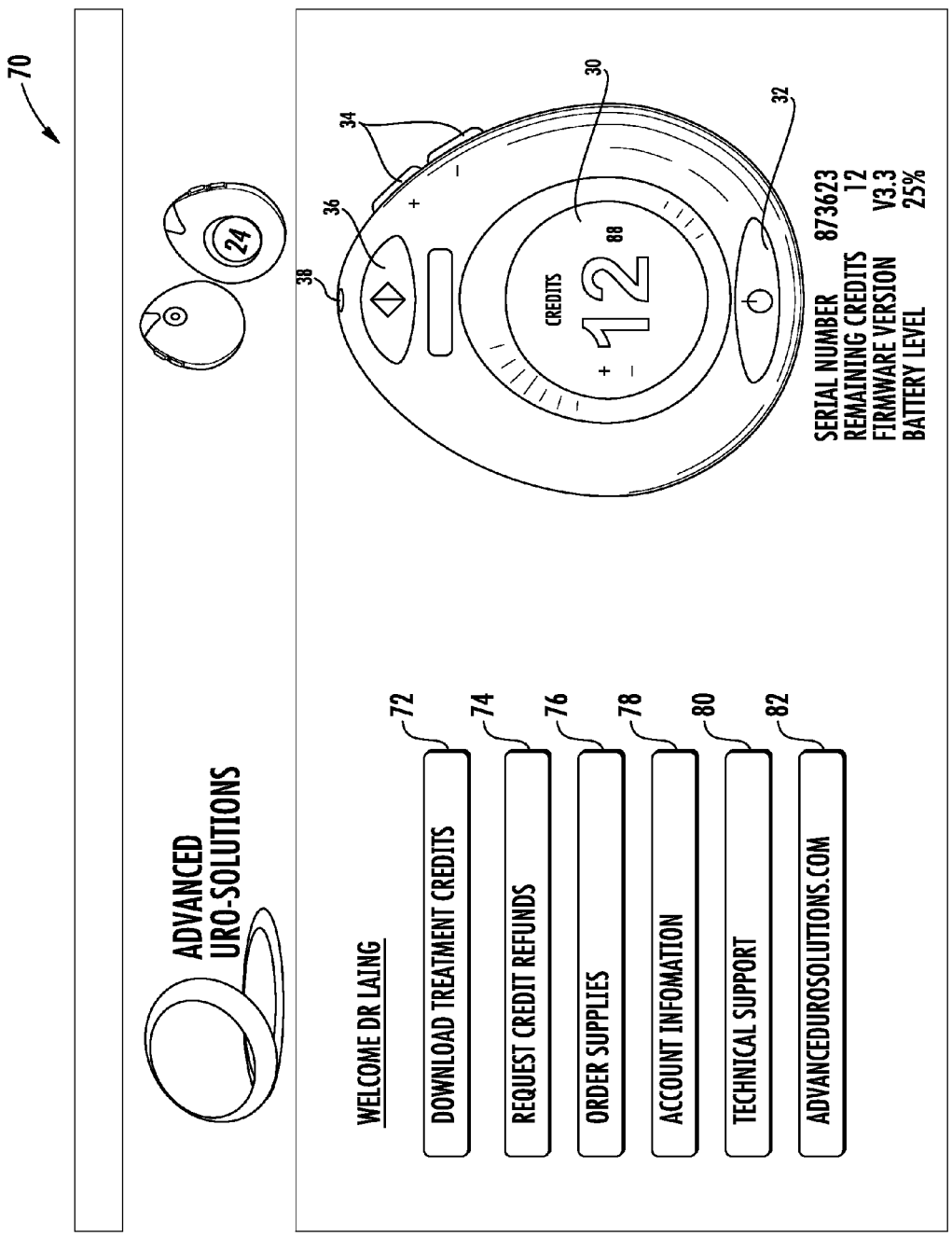
FIG. 6 is a view of a customer interface according to one embodiment of the disclosure.

Referring to FIG. 6, the computer system includes a customer interface 70 for purchasing treatment credits to be used with an appropriate neurostimulator unit 16. It should be understood that the customer could include the patient or a health care professional or office that administers treatment sessions to patients, and the terms user, customer, patient, and administrator may be used interchangeably herein. Each customer is set up with a customer account and the customer's neurostimulator unit or units 16 are then linked to this account. The customer interface 70 is preferably available to the customer through a web based application accessible from a desktop computer, laptop, tablet computer, smartphone, or the like.

As shown in FIG. 6, the customer has several options to choose from through the customer interface 70 such as downloading and purchasing treatment credits 72, requesting a refund of treatment credits 74, ordering supplies 76 such as electrode pads 12 and needle electrodes 14, accessing account information 78, requesting technical support 80, and one or more links 82 that redirect the user to additional information on the web such as the manufacturer website.

When the neurostimulator unit 16 is connected to the computer system, the microcontroller is updated, preferably automatically, based on the actions of the customer through the customer interface 70. For example, if the user purchases a treatment credit using the customer interface 70, the purchased treatment credit is transferred to the microcontroller of the neurostimulator unit 16 for providing the user with an additional treatment session when the unit 16 is connected to the computer system or a network connected to the computer system.

Figure 7:
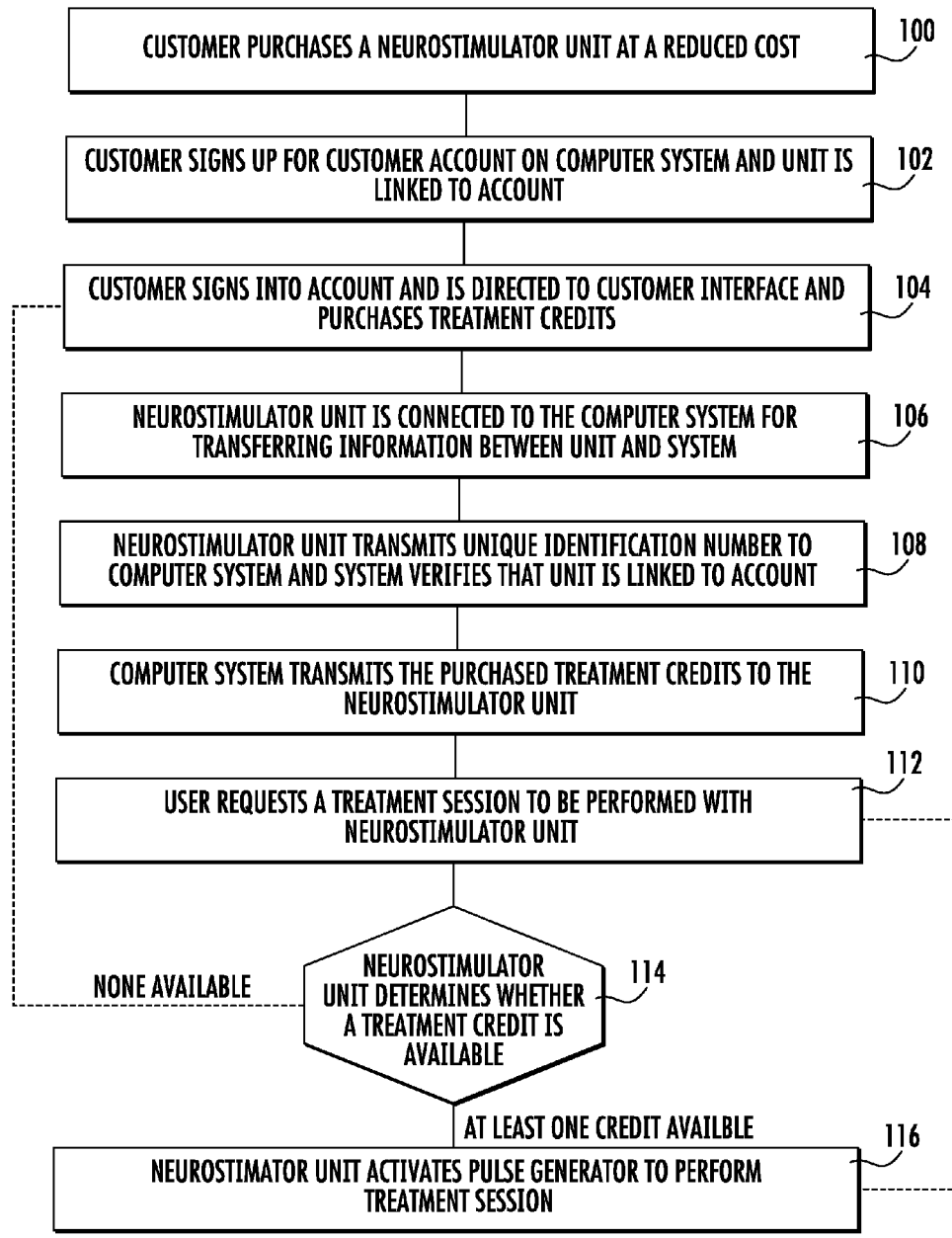
FIG. 7 is a flow chart of a method for performing treatment sessions using a neurostimulator unit according to one embodiment of the disclosure.

Referring to FIG. 7, a method for performing tibial nerve stimulation treatment sessions using the nerve stimulation device 10 is provided. It should be understood that the following steps are generally performed in no particular order and some steps may be omitted. In step 100, the user or customer is provided with a nerve stimulation device 10 having a neurostimulator unit 16 as described substantially above. Preferably, the nerve stimulation device 10 is provided to the customer at a reduced cost which is to be recouped by having the customer pay for using the device 10 on a per-treatment session basis. In step 102, the customer signs up for a customer account on the computer system and links the customer's one or more neurostimulator units 16 with the customer account. Preferably, each neurostimulator unit 16 includes a unique identification number and the neurostimulator unit 16 is linked to the customer account by providing the appropriate unique identification number.

After signing into the customer account, the customer is directed to the customer interface 70 and purchases one or more treatment credits in step 104. Each purchased treatment credit preferably includes a unique serial number for assisting in tracking usage of the treatment credit. In step 106, the neurostimulator unit 16 is connected to the computer system through a wireless or hardwire connection as described above for transferring information between the neurostimulator unit 16 and the computer system. In step 108, the neurostimulator unit 16 transmits its unique identification number to the computer system and the computer system verifies that the unit 16 is linked to the customer account.

After verification that the unit 16 is an authorized device for the particular customer account, the computer system transmits the one or more treatment credits purchased in step 104 to the neurostimulator unit 16 in step 110. Alternatively, the information could be transferred between the computer system and the neurostimulator unit using a digital storage device such as a flash drive. In addition to transmitting the purchased treatment credits to the neurostimulator unit 16, information transferred to the computer system from the neurostimulator unit 16 could include a number of remaining treatment credits, if any, available to the unit 16, the total number of treatment sessions provided by the unit 16, the status of incomplete treatment sessions performed by the unit 16, usage information of particular treatment credits based on the treatment credit's unique serial number, battery status, etc. This information can then be accessed from the customer interface 70 for monitoring the status and usage of the neurostimulator unit 16 when desired. For example, the usage information would be helpful when preparing bills to patients and processing insurance claims.

In step 112, the patient or administrator requests a treatment session to be performed using the neurostimulator unit 16. At this point, the unit may or may not be connected to the computer system. In step 114, the neurostimulator unit 16 determines whether a treatment credit is available. If it is determined in step 114 that there the unit 16 has no more available treatment credits, the patient or user must return to step 104 to purchase additional treatment credits before another treatment session may be performed. If a treatment credit is available, the nerve stimulation device 10 performs a treatment session using one of the treatment credits purchased in step 104 and transferred to the neurostimulator unit in step 116. In performing the treatment session, the unit 16 activates the pulse generator so that current pulses traverse the stimulation site during the treatment session by passing from the transcutaneous electrode 12 to the internal percutaneous electrode needle 14. After a treatment session is performed, the number of available treatment credits is reduced by one. Step 112 is then repeated when another treatment session is requested.

The foregoing description of preferred embodiments for this disclosure have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for providing a reusable nerve stimulation system to treat incontinence, the method comprising:
   providing a computer system having a customer interface;
   providing a neurostimulator unit including:
      a pulse generator for electrically coupling to a transcutaneous electrode configured to be applied to skin adjacent a stimulation site of a patient and a percutaneous electrode having a leading end for inserting adjacent the stimulation site of a patient, and
      a microcontroller in communication with the pulse generator for monitoring a number of available treatment credits to the neurostimulator unit and for activating the pulse generator during a treatment session when the number of available treatment credits is at least one;
   receiving at the computer system a treatment credit request transmitted through the customer interface, each treatment credit request having purchase information including a number of treatment credits purchased, each treatment credit purchased corresponding to an available treatment credit;
   transmitting the number of treatment credits purchased to the microcontroller of the neurostimulator unit; and
   adjusting the number of treatment credits available to the neurostimulator unit based on the number of treatment credits purchased transmitted to the microcontroller of the neurostimulator unit.

2. The method of claim 1 further comprising:
   determining whether the number of available treatment credits is at least one; and
   activating the pulse generator based on a treatment session request when it is determined that the number of available treatment credits is at least one.

3. The method of claim 1 further comprising:
   transmitting usage information from the microcontroller to the computer system, the usage information including a number of treatment sessions performed;
   monitoring the usage information of the neurostimulator unit through the computer system; and
   providing the usage information to a customer through a customer interface of the computer system.

4. The method of claim 1 further comprising:
   providing each treatment credit purchased with a unique serial number;
   monitoring usage information of each treatment credit purchased at the neurostimulator unit;
   transmitting the usage information from the neurostimulator unit to the computer system for each treatment credit purchased based on the unique serial number.

5. The method of claim 1 wherein the pulse generator is dimensioned and configured to be removeably attached to the transcutaneous electrode.

6. The method of claim 1 wherein the computer system transmits the number of treatment credits purchased to the microcontroller wirelessly through one of radio frequency, Bluetooth, infrared, and a wireless internet connection.

7. The method of claim 1 wherein the computer system transmits the number of treatment credits purchased to the microcontroller through a universal serial bus connection.

8. A method for providing a reusable nerve stimulation system to treat incontinence, the method comprising:
- providing at least one neurostimulator unit to a customer, each neurostimulator unit including:
  - a pulse generator for electrically coupling to a transcutaneous electrode configured to be applied to skin adjacent a stimulation site of a patient and a percutaneous needle electrode having a removable leading end for inserting adjacent the stimulation site of the patient, and
  - a microcontroller in communication with the pulse generator for monitoring a number of available treatment credits to the neurostimulator unit;
- linking each of the neurostimulator units to a customer account, the customer able to access the customer account through a customer interface of a computer system;
- receiving at the computer system a treatment credit request from the customer transmitted through the customer interface, the treatment credit request having purchase information including a number of treatment credits purchased to be stored in the customer account;
- connecting at least one of the neurostimulator units to the computer system;
- transmitting at least one of the treatment credits purchased from the customer account to the microcontroller of the connected neurostimulator unit;
- adjusting the number of available treatment credits to the neurostimulator unit and the number of treatment credits purchased stored in the customer account based on the number of treatment credits purchased transmitted to the microcontroller; and
- activating the pulse generator upon request by the customer to generate current pulses that pass between the transcutaneous electrode and the percutaneous electrode for providing stimulation to the stimulation site during one or more treatment sessions, the pulse generator able to be activated only when the number of available treatment credits to the neurostimulator unit is at least one.

9. The method of claim 8 further comprising:
- transmitting usage information from the microcontroller to the computer system, the usage information including a number of treatment sessions performed;
- monitoring the usage information of the neurostimulator unit through the computer system; and
- providing the usage information to the customer through the customer interface of the computer system.

10. The method of claim 8 further comprising attaching the pulse generator to the transcutaneous electrode prior to activating the pulse generator.

11. The method of claim 10 further comprising providing a handheld unit for wirelessly communicating the activation request to the neurostimulator unit.

12. The method of claim 8 wherein the connecting of the neurostimulator unit and computer system and the transmitting of the treatment credits purchased from the customer account to the microcontroller of the connected neurostimulator unit is performed wirelessly.

13. The method of claim 8 further comprising inserting the leading end of the percutaneous needle electrode adjacent the stimulation site of the patient, the stimulation site being adjacent a tibial nerve.

* * * * *